United States Patent
Beith et al.

(10) Patent No.: US 10,226,336 B2
(45) Date of Patent: Mar. 12, 2019

(54) STENTED PROSTHETIC HEART VALVE

(71) Applicant: Medtronic, Inc., Minneapolis, MN (US)

(72) Inventors: Jason Beith, Santa Ana, CA (US); Elliot Howard, Aliso Viejo, CA (US)

(73) Assignee: Medtronic, Inc., Minneapolis, MN (US)

( * ) Notice: Subject to any disclaimer, the term of this patent is extended or adjusted under 35 U.S.C. 154(b) by 102 days.

(21) Appl. No.: 15/206,463

(22) Filed: Jul. 11, 2016

(65) Prior Publication Data

US 2016/0331530 A1    Nov. 17, 2016

Related U.S. Application Data

(63) Continuation of application No. 14/063,705, filed on Oct. 25, 2013, now Pat. No. 9,414,913.

(51) Int. Cl.
*A61F 2/24* (2006.01)

(52) U.S. Cl.
CPC .......... *A61F 2/2418* (2013.01); *A61F 2/2409* (2013.01); *A61F 2230/0008* (2013.01); *A61F 2230/0019* (2013.01)

(58) Field of Classification Search
CPC .................................................... A61F 2/2409
See application file for complete search history.

(56) References Cited

U.S. PATENT DOCUMENTS

| | | | |
|---|---|---|---|
| 3,491,376 A * | 1/1970 | Shiley | A61F 2/2409 623/2.38 |
| 3,714,671 A | 2/1973 | Edwards et al. | |
| 4,106,129 A | 8/1978 | Carpentier et al. | |
| 4,501,030 A | 2/1985 | Lane | |
| 5,549,665 A | 8/1996 | Vesely et al. | |
| 5,928,281 A | 7/1999 | Huynh et al. | |
| 5,935,163 A | 8/1999 | Gabbay | |
| 6,102,994 A | 8/2000 | Zhou et al. | |
| 6,231,602 B1 | 5/2001 | Carpentier et al. | |
| 6,338,740 B1 | 1/2002 | Carpentier | |

(Continued)

FOREIGN PATENT DOCUMENTS

| | | |
|---|---|---|
| WO | WO2004/026173 | 4/2004 |
| WO | WO2005/097003 | 10/2005 |
| WO | WO2006/108090 | 10/2006 |

*Primary Examiner* — Brian Pellegrino (74) *Attorney, Agent, or Firm* — Dicke, Billig & Czaja, PLLC (57) ABSTRACT

A stented prosthetic heart valve including a stent assembly, a leaflet assembly, and mounting members. The stent assembly includes a stent post frame, a stent post frame covering, and a base frame. The stent post frame includes a continuous rail forming a closed-curved shape defining a longitudinal axis, and a plurality of circumferentially-spaced posts projecting from cusp segments in a direction of the longitudinal axis. The cloth covering encompasses the rail. The base frame supports the cusp segments. The valve leaflet assembly is attached to the stent assembly, and includes a leaflet clamped between one of the cusp segments and the base frame. The mounting members each directly pass through the stent post frame cloth covering, the first leaflet and the base frame. The rail can have a constant cross-sectional shape with a major axis dimension that is greater than a minor axis dimension.

10 Claims, 13 Drawing Sheets

(56) References Cited

U.S. PATENT DOCUMENTS

| | | |
|---|---|---|
| 6,350,282 B1 | 2/2002 | Eberhardt |
| 6,454,799 B1 | 9/2002 | Schreck |
| 6,461,382 B1 | 10/2002 | Cao |
| 6,539,984 B2 | 4/2003 | Lam |
| 6,558,418 B2 | 5/2003 | Carpentier et al. |
| 6,585,766 B1 | 7/2003 | Huynh et al. |
| 6,733,525 B2 | 5/2004 | Yang et al. |
| 6,736,845 B2 | 5/2004 | Marquez et al. |
| 6,945,997 B2 | 9/2005 | Huynh et al. |
| 7,137,184 B2 | 11/2006 | Schreck |
| 7,252,681 B2 | 8/2007 | Berg et al. |
| 7,374,571 B2 | 5/2008 | Pease et al. |
| 7,399,315 B2 | 7/2008 | Iobbi |
| 7,455,689 B2 | 11/2008 | Johnson |
| 7,473,275 B2 | 1/2009 | Marquez |
| 7,481,838 B2 | 1/2009 | Carpentier et al. |
| 7,556,646 B2 | 7/2009 | Yang et al. |
| 7,682,391 B2 | 3/2010 | Johnson |
| 7,739,971 B2 | 6/2010 | Chambers et al. |
| 7,758,640 B2 | 7/2010 | Vesely |
| 7,776,084 B2 | 8/2010 | Johnson |
| 7,871,435 B2 | 1/2011 | Carpentier et al. |
| 8,062,359 B2 | 11/2011 | Marquez et al. |
| 8,219,229 B2 | 7/2012 | Cao et al. |
| 8,276,533 B2 | 10/2012 | Chambers et al. |
| 8,845,720 B2 * | 9/2014 | Conklin ............... A61F 2/2412 623/2.14 |
| 9,468,527 B2 * | 10/2016 | Marquez ............... A61F 2/2445 |
| 2002/0055775 A1 | 5/2002 | Carpentier et al. |
| 2006/0136052 A1 | 6/2006 | Vesely |
| 2006/0229718 A1 | 10/2006 | Marquez |
| 2008/0294247 A1 | 11/2008 | Yang et al. |
| 2008/0294248 A1 | 11/2008 | Yang et al. |
| 2011/0167603 A1 * | 7/2011 | Vesely ................. A61F 2/2427 29/221.6 |
| 2011/0190878 A1 | 8/2011 | Shu et al. |
| 2011/0276128 A1 | 11/2011 | Cao et al. |
| 2011/0282440 A1 | 11/2011 | Cao et al. |
| 2012/0078357 A1 | 3/2012 | Conklin |
| 2012/0296418 A1 | 11/2012 | Bonyuet et al. |
| 2015/0289972 A1 | 10/2015 | Yang |

\* cited by examiner

STENTED PROSTHETIC HEART VALVE

RELATED APPLICATIONS

This application is a Continuation of and claims the benefit of U.S. patent application Ser. No. 14/063,705 filed Oct. 25, 2013, now allowed. The disclosures of which are herein incorporated by reference in their entirety.

BACKGROUND

The present disclosure relates to implantable prosthetic heart valves. More particularly, it relates to prosthetic heart valves incorporating a stent and methods of manufacture thereof.

Various types and configurations of prosthetic heart valves are used to replace diseased natural human heart valves. The actual shape and configuration of any particularly prosthetic heart valve is dependent to some extent upon the valve being replaced (i.e., mitral valve, tricuspid valve, aortic valve, or pulmonary valve). In general, the prosthetic heart valve designs attempt to replicate the function of the valve being replaced and thus will include valve leaflet-like structures used with either bioprosthesis or mechanical heart valves prosthesis.

As used throughout the specification, a "prosthetic heart valve" is intended to encompass bioprosthetic heart valves having leaflets made of a biological material (e.g., harvested porcine valve leaflets, or bovine or equine pericardial leaflets), along with synthetic leaflet materials or other materials. Bioprosthetic valves are divided into two broadly defined classes; namely, stentless and stented prosthetic heart valves. Stentless bioprosthetic heart valves do not have a support frame. Rather, the biological valve member is sutured to a flexible cloth material. The hemodynamics of a stentless valve may more closely approximate that of a natural heart valve. A drawback of a stentless valve, however, is that it is more difficult to implant into the patient than a stented valve. Furthermore, a stentless valve can be collapsed and deformed by the action of the heart because it has no support structure. The action of the heart muscles on this type of valve can fold the valve material and create unexpected stress risers that can eventually lead to failure.

Stented bioprosthetic heart valves have a frame (or stent) to which the biological valve material is attached. The biological valve members are sutured to the stent that provides support for the valve member in the patient's body. The stent prevents the biological valve members from collapsing and simplifies the insertion of the valve into the annulus of the patient after excision of the diseased valve. The stented bioprosthetic valve imitates the natural action of heart valves and provides a structure that is relatively compatible with the cardiovascular system. Stented prosthetic heart valves are believed to have important clinical advantages over mechanical or non-tissue prosthetic valves.

Known stent constructions for stented bioprosthetic heart valves comprise two or three support structures, commonly referred to as stent posts or commissure posts, projecting from a base frame or ring. The stent or commissure posts define the juncture between adjacent tissue or synthetic leaflets otherwise secured thereto, and are typically linear in projection from the base frame. With some stent configurations, the stent posts are provided by a stent post frame that in turn is assembled to the base frame, with the two components collectively providing the completed stent. The shape of the stent post frame is generated by a continuous support rail or wire (sometimes referred to as a "wireform") that is made of either a steel alloy or thermoplastic material, and a plastic wall. The support rail typically is circular in cross-section, and formats the stent post frame shape to interpose the stent posts between lower cusp portions. The base frame generally conforms to the shape of the stent post frame for attachment to the cusp portions, and provides rigid support in the lateral direction. A covering of porous biocompatible cloth is fitted about the stent, completely enclosing the stent post frame and the base frame. The cloth cover provides a sewing attachment point for the leaflet commissures and cusps. In some constructions, a cloth-covered suture ring or sewing cuff can be attached to the cloth-covered stent for sewing of the prosthetic valve within the patient's heart.

Most currently-available prosthetic heart valve stents (and in particular the stent post frame thereof) are geometrically formed from a devolved cylinder. That is to say, a right circular cylinder cut in such a way as to have a plurality of stent post tips adjacent to some parabolic/elliptic scallops, forming the leaflet attachment or margin of attachment. As a consequence of this design, the cross-section of any horizontal plane changes from right rectangular to arc-like, resulting in a very high non-linear increase in cross-sectional inertia as well as eccentricity of the neutral axis from the stent post tip to the cusp of the leaflet. The structural implications of this are two-fold. Firstly, there is considerably more radial rigidity in the lower sections of the stent as compared to the upper sections, and as a direct consequence of the rigidity and neutral axis eccentricity, the lower sections will be considerably more stressed than the upper sections. This structural configuration also represents a challenge for the leaflets, as the top of the stent post frame is allowed to deflect more radially than the base, and as a result the leaflets have a very non-linear distribution of radial deflection, and hence demand, from the stent post downwardly.

The manner in which the stent post frame is attached to the base frame, as well as attachment of the leaflets to the collective stent, can also problematically affect responsiveness of the stented prosthetic heart valve to various forces following implant. For example, if the stent post frame is rigidly connected to, and thus rigidly constrained by, the base frame, a considerable concentration of demand is exerted at the junction of the stent post frame with the base frame.

In light of the above, a need exists for stented prosthetic heart valve exhibiting uniform stress demand and a smooth, continuous bend of the linear stent post.

SUMMARY

Some aspects of the present disclosure relate to a stented prosthetic heart valve including a stent assembly, a valve leaflet assembly, and a plurality of mounting members. The stent assembly includes a stent post frame, a stent post frame cloth covering, and a base frame. The stent post frame includes a continuous rail forming a closed-curved shape defining a central longitudinal axis, and a plurality of circumferentially spaced posts projecting from, and interposed between, cusp segments in a direction of the longitudinal axis. The stent post frame cloth covering encompasses the stent post frame. The base frame is configured to support the cusp segments of the stent post frame, and is connected to the stent post frame via the mounting members. The valve leaflet assembly is attached to the stent assembly, and includes a first leaflet clamped between a first one of the cusp segments and the base frame. The mounting members secure the first leaflet to the stent assembly, each passing directly through the stent post frame cloth covering, the first leaflet and the base frame. In some embodiments, the mounting members are sutures. In other embodiments, the base frame includes a hub and a support wall projecting transversely outwardly from the hub. The support wall defines a plurality of holes for receiving respective ones of mounting members.

In other embodiments, each of the posts is defined by spaced apart leg portions extending from corresponding ones of the cusp segments and intersecting at a tip opposite the cusp segments. Further, the rail has a constant cross-sectional shape along at least the posts, with the cross-sectional shape defining a major axis dimension that is greater than a minor axis dimension. With these constructions, the bending inertia and rigidity of the stent assembly is generally uniform at all locations, promoting a linear deflection response in the posts. In related embodiments, the shape of the stent post frame effectuates a rotation of approximately 90 degrees of the minor axis dimension relative to a plane radially normal to the central longitudinal axis in transitioning from each of the leg portions to the corresponding tip.

DETAILED DESCRIPTION

Figure 1:
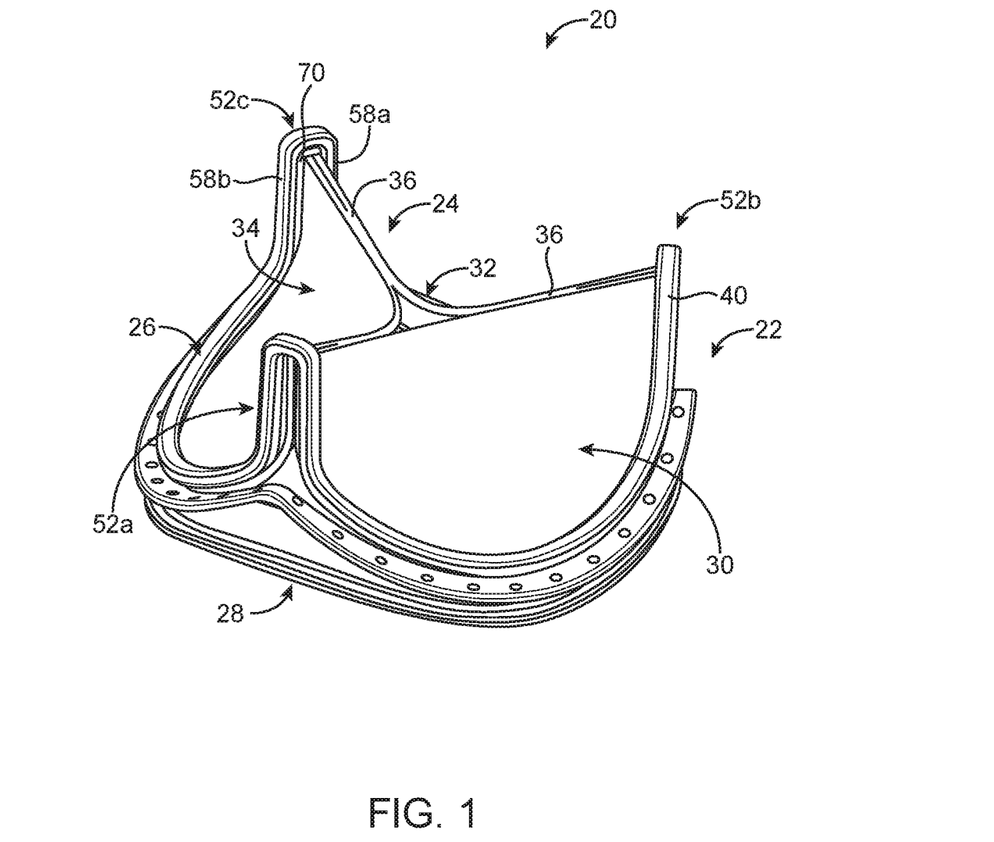
FIG. 1 is a perspective view of a portion of a stented prosthetic heart valve in accordance with principles of the present disclosure.

One embodiment of a stented prosthetic heart valve 20 in accordance with principles of the present disclosure is shown in FIG. 1. The prosthetic heart valve 20 includes a stent assembly 22 and a biological valve leaflet assembly 24. The stent assembly 22 includes a stent post frame 26 and a base frame 28. The stent post frame 26 and the base frame 28 are each covered by a separate cloth covering (omitted from the view of FIG. 1 for ease of illustration) such that the cloth covered stent post frame 26 and the cloth covered base frame 28 collectively define the stent assembly 22. The valve leaflet assembly 24 can assume various forms, and generally includes tissue or synthetic leaflets 30-34 that are integrally attached to the stent assembly 22. The leaflets 30-34 converge axially along commissures 36. Although in the embodiment illustrated the prosthetic heart valve 20 has three of the leaflets 30-34 and three of the commissures 36, it should be understood that the concepts disclosed herein will be equally applicable to a valve having two, or more than three, of the leaflets 30-34 (and corresponding number of the commissures 36). A suture or sewing ring (not shown) is optionally provided and attaches around the outside of the base frame 28. Where provided, the sewing ring serves as a platform through which attachment structures (e.g., sutures, staples, clips, etc.) may be passed to hold the prosthetic heart valve 20 in place within the body.

The stent post frame 26 is defined by or includes a continuous rail 40. In an exemplary construction of the prosthetic heart valve 20, the peripheral edges of the leaflets 30-34 are directly connected to the rail 40 (via the covering (not shown) surrounding the rail 40), and therefore the rail 40 defines the shape of the flow orifice and the three-dimensional support structure for the leaflets 30-34. Further, a contour of the rail 40 defines the leaflet axial dimension and thus deflection of the commissures 36.

With the above in mind, one embodiment of the stent post frame 26 in accordance with principles of the present disclosure is shown in isolation in FIGS. 2A-2D. The rail 40 is a continuous member forming a closed-curve shape (or "wireform shape"). In general terms, the closed-curve shape of the stent post frame 26 is generally annular, and defines a central longitudinal axis $L_A$. Further, the stent post frame 26 defines or forms alternating, circumferentially-spaced stent or commissure posts 52a, 52b, 52c and lower or cusp segments 54a, 54b, 54c. The stent posts 52a-52c can be identical and each comprise relatively narrow portions extending from adjacent ones of the cusp segments 54a-54c in a direction of the longitudinal axis $L_A$ and terminating in a closed, slightly arcuate tip 56a-56c longitudinally opposite the cusp segments 54a-54c. Each of the stent posts 52a-52c is defined by spaced apart leg portions or cantilevers 58a, 58b each extending from a corresponding one of the cusp segments 54a-54c and intersecting at the corresponding tip 56a-56c. As best reflected in FIGS. 2C and 2D, the stent posts 52a-52c can generally follow the circular shape collectively defined by the cusp segments 54a-54c and are substantially linear (e.g., within 5% of a truly linear arrangement). In other embodiments, the stent posts 52a-52c can extend at an angle (or rake angle) slightly radially inwardly from the adjacent cusp segments 54a-54c to the corresponding tip 56a-56c so that the stent post frame 26 defines an approximately conical shape. The cusp segments 54a-54c are continuously curved and have relatively large radii. As best reflected by FIGS. 2A and 2B, the continuously-curved nature of the cusp segments 54a-54c can include a curvature in the longitudinal direction. For example, each of the cusp segments 54a-54c has a convex curved shape parallel to the longitudinal axis $L_A$ in extension between the corresponding stent posts 52a-52c, centered about a center point 60 defined along each of the cusp segments 54a-54c.

Figure 3A:
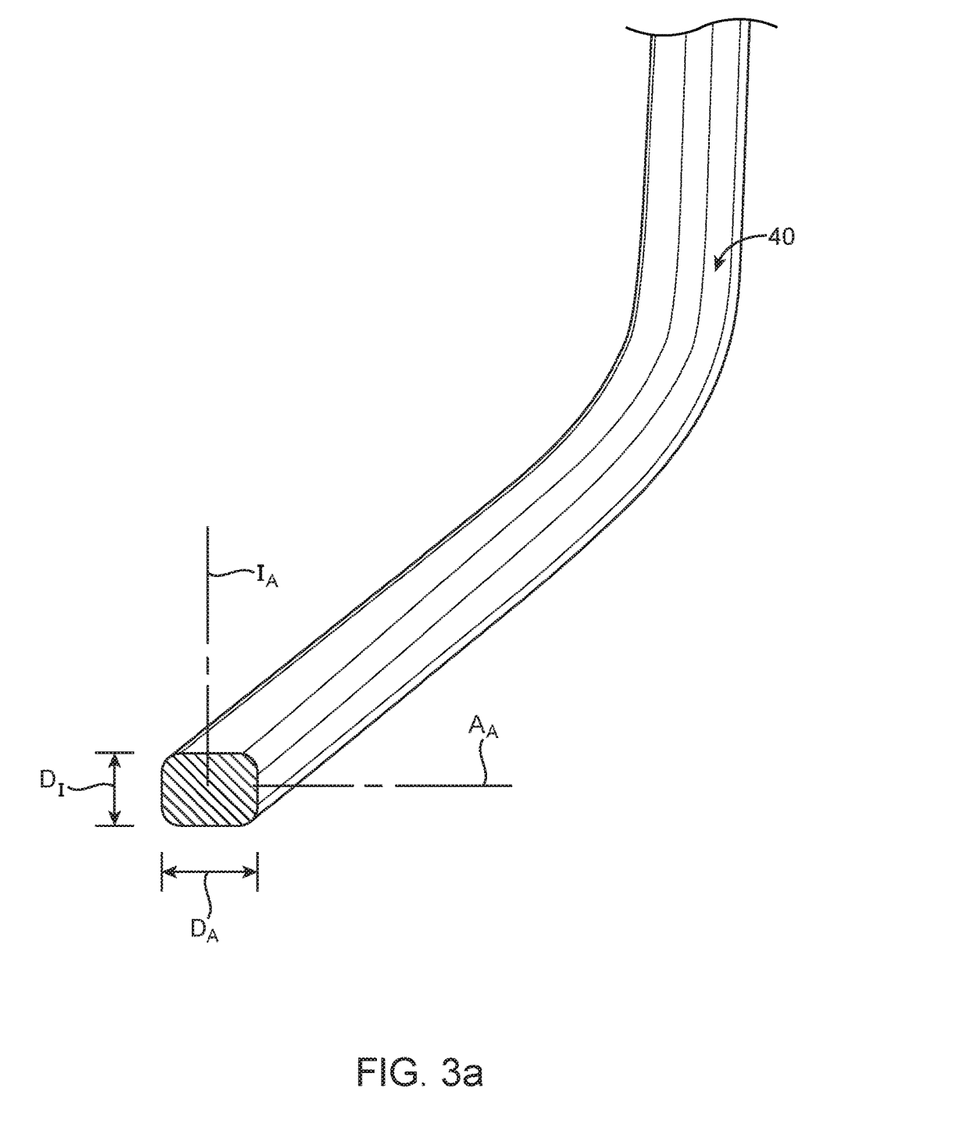
FIG. 3A is an enlarged, cross-sectional view of a portion of the stent post frame of FIG. 2A.
Figure 3B:
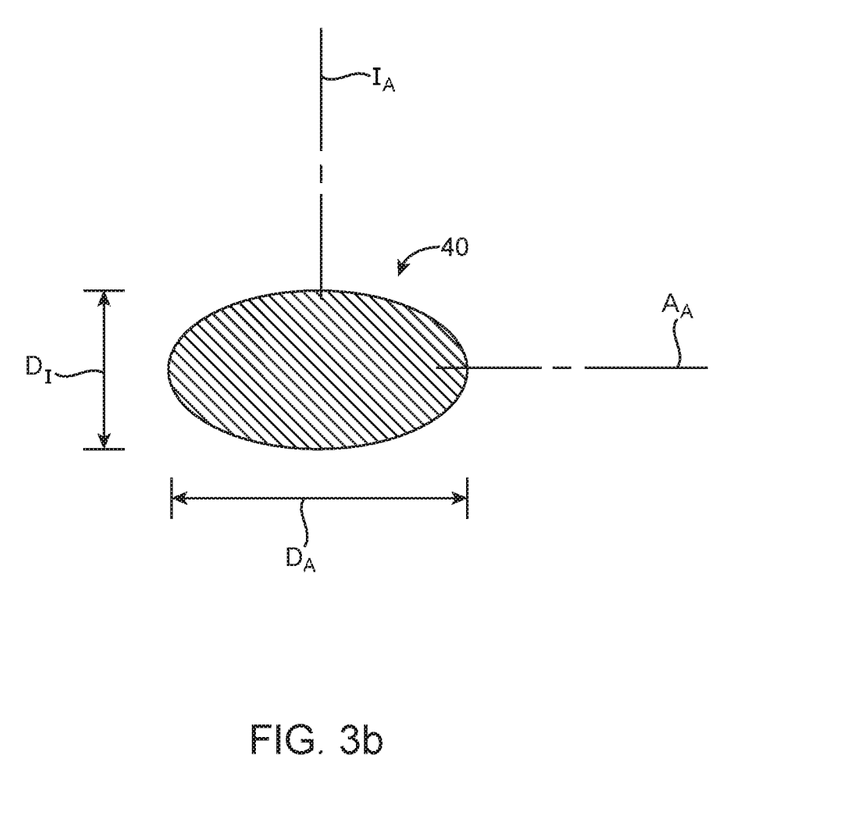
FIG. 3B is a simplified cross-sectional view of a rail component of another embodiment stent post frame in accordance with principles of the present disclosure.

The rail 40 has, in some embodiments, a uniform cross-sectional shape along at least the stent posts 52a-52c, and optionally along an entirety of the stent post frame 26. With additional reference to FIG. 3A, the cross-sectional shape of the rail 40 defines a major axis $A_A$ and a minor axis $I_A$. The major axis dimension of the cross-sectional shape, $D_A$, is greater than the minor axis dimension $D_I$. For example, the uniform cross-sectional shape of the rail 40 can be rectangular as shown. The rectangular cross-sectional shape is arranged radially normal to the central longitudinal axis $L_A$, and is exactly the same from the tips 56a-56c at least to the cusp segments 54a-54c in some embodiments. This arrangement better ensures that bending inertia and rigidity of the stent post frame 26 is the same at all sections, thus allowing for a linear deflection response in each of the stent posts 52a-52c. A wide variety of other cross-sectional shapes having a major axis dimension $D_A$ greater than a minor axis dimension $D_I$ are also envisioned by the present disclosure. For example, the cross-sectional shape of the rail 40 can be an oval as shown in FIG. 3B. Other cross-sectional shapes such as parallelograms, irregular shapes, etc., are also acceptable. However, rails in accordance with the present disclosure do not have a cross-sectional shape that is a circle or square.

Figure 4A:
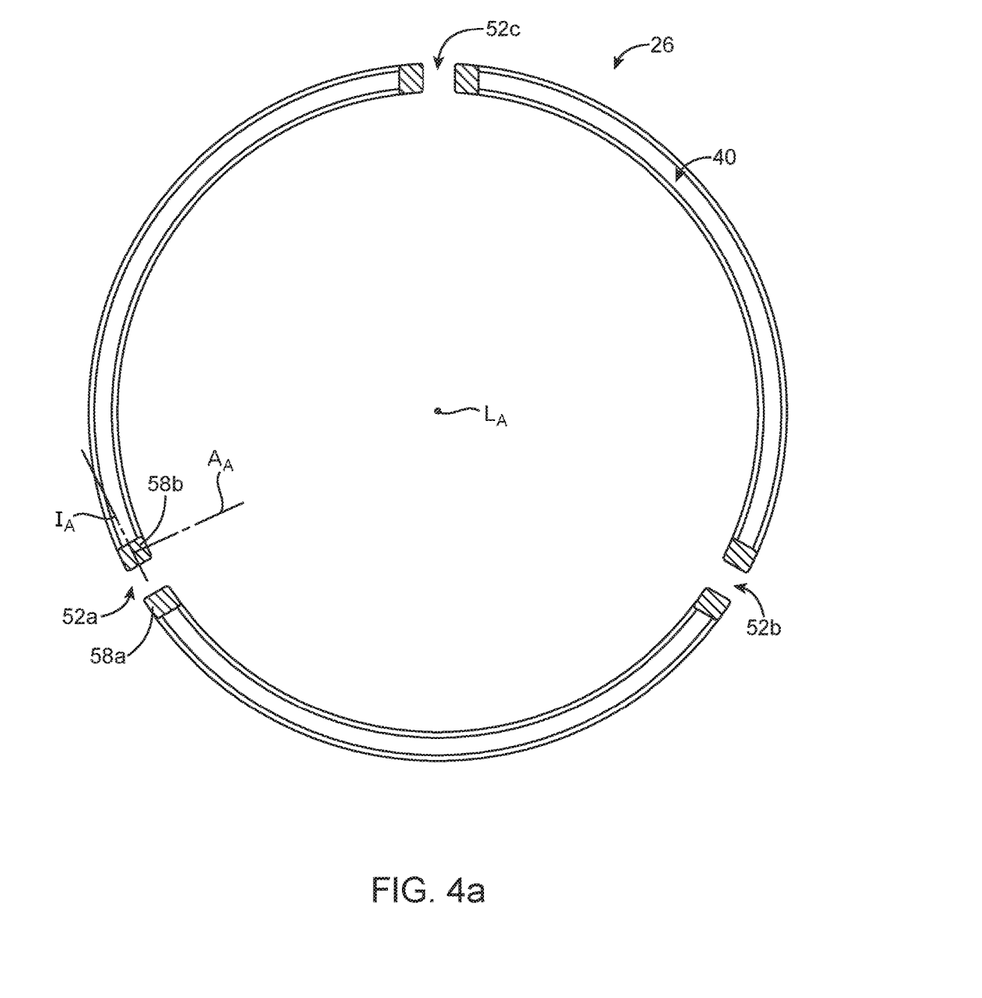
FIG. 4A is a cross-sectional view of the stent post frame of FIG. 2A along a plane perpendicular to a central longitudinal axis of the stent post frame.
Figure 4B:
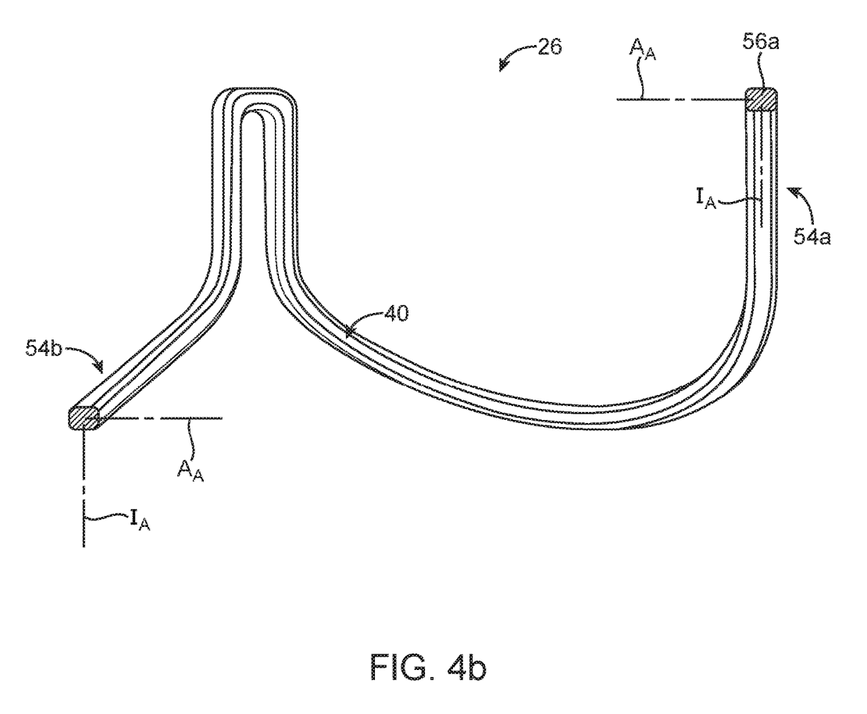
FIG. 4B is a cross-section view of the stent post frame of FIG. 2A along a plane normal to the central longitudinal axis of the stent post frame.

Returning to FIG. 2A, although the cross-sectional shape of the rail 40 is constant along an entirety of the at least the stent posts 52a-52c, a spatial arrangement of the major and minor axis dimensions $D_A$, $D_I$ (FIG. 3A) is not constant. More particularly, the cross-sectional shape of the rail 40 is rotated approximately 90 degrees (e.g., plus or minus 5 degrees) along each of the stent posts 52a-52c at the corresponding tips 56a-56c, and from the stent posts 52a-52c to each of the cusp segments 54a-54c to keep the minor axis dimension $D_I$ perpendicular to the margin of attachment to the base frame 28 (FIG. 1). For example, FIG. 4A illustrates a cross-section of the stent post frame 26 in a plane perpendicular to the longitudinal axis $L_A$ and passing through each of the stent posts 52a-52c (referenced generally). The major and minor axes $A_A$, $I_A$ of the rail 40 cross-sectional shape are identified along the first stent post 52a. The cross-sectional shape of the rail 40 along the legs 58a, 58b arranges the minor axis $I_A$ to be essentially tangential to the longitudinal axis $L_A$, and the major axis $A_A$ to be essentially perpendicular to the longitudinal axis $L_A$. FIG. 4B illustrates a cross-section of the stent post frame 26 is a plane normal or parallel to the longitudinal axis $L_A$ and passing through the tip 56a of one of the stent posts 52a and through one of the corresponding cusp segments 54b. A comparison of FIGS. 4A and 4B reveals that the approximately 90 degree turn at the tip 56a spatially arranges the cross-sectional shape of the rail 40 such that the minor axis $I_A$ is approximately parallel to the longitudinal axis $L_A$, while the major axis $A_A$ remains essentially perpendicular to the longitudinal axis $I_A$. Further, at the cusp segment 54b, the minor axis $I_A$ is essentially perpendicular to the longitudinal axis $L_A$.

Figure 5:
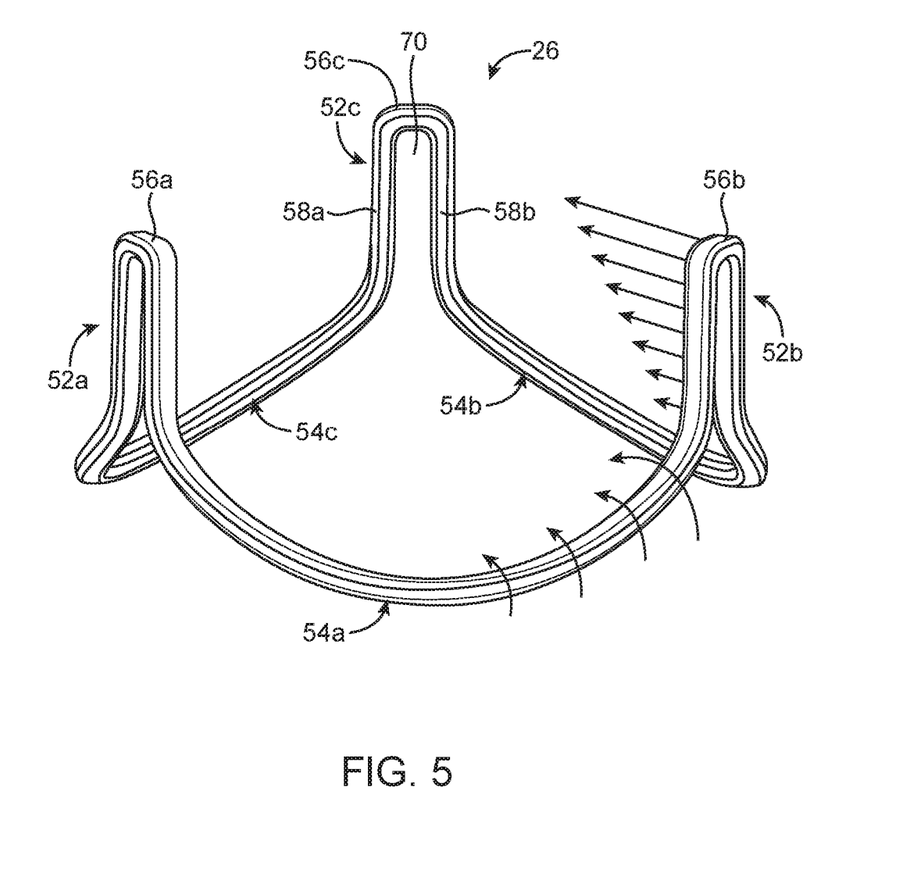
FIG. 5 is a perspective view of the stent post frame of FIG. 2A and illustrating deflection and inertia response characteristics.

With the above construction, the stent post frame 26 responds to applied forces by bending as a "wish bone" whereby the stent posts 52a-52c bend linearly at and adjacent the corresponding tips 56a-56c; the rail 40 exhibits a combined flexural and torsional response at the cusp segments 54a-54c and along the stent posts 52a-52c in a region immediately adjacent the cusp segments 54a-54c. The level of resistance to torque increases from the stent posts 52a-52c to the center point 60 of each of the cusp segments 54a-54c. These differing deflection and bending responses are identified by arrows in the view of FIG. 5, with a length of each arrow reflecting a magnitude of free movement. An inner gap 70 between the two vertical leg portions or cantilevers 58a, 58b of each of the stent posts 52a-52c acts to increase the circumferential stiffness of the stent post frame 26. In other embodiments, this circumferential stiffness can be further increased by raking the leg portions 58a, 58b in a direction of the base frame 28 (FIG. 1). However, because the leg portions 58a, 58b are stitched together and the gap 70 filled by tissue/fabric, lateral rigidity is provided as in-plane shear strength through the corresponding tip 56a-56c; thus, a significant rake angle is not necessary in some embodiments.

Returning to FIG. 4B, in addition to promoting a desired bending response along an entirety of the stent post frame 26, the spatial arrangement of the rail 40 cross-sectional shape along the cusp segments 54a-54c promotes interface with the base frame 28 (FIG. 1). By arranging the cross-sectional shape of the rail 40 along the cusp segments 54a-54c as described above, the major axis $A_A$ is parallel with the zone of attachment to the base frame 28, with the major axis dimension $D_A$ (FIG. 3A) providing a substantive surface area interface with the base frame 28. Stated otherwise, the minor axis dimension $D_I$ (FIG. 3A) is held substantially perpendicular to the margin of attachment to the base frame 28.

Figure 6A:
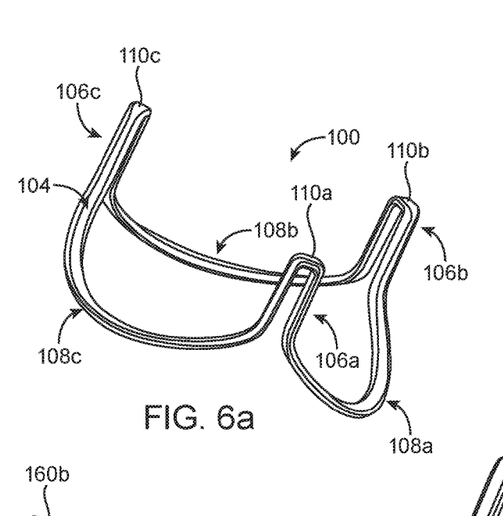
FIG. 6A is a perspective view of another stent post frame useful with the stented prosthetic heart valve of FIG. 1.

The stent post frame 26 described above is but one embodiment envisioned by the present disclosure. For example, FIG. 6A illustrates another embodiment stent post frame 100 useful with the stented prosthetic heart valves of the present disclosure. The sent post frame 100 is akin to the stent post frame 26 (FIG. 2A), and has a continuous, closed-curve shape generated by a rail 104. The closed-curve shape includes three (optionally two) stent posts 106a-106c interposed between cusp segments 108a-108c. As compared to the stent post frame 26 of previous embodiments, the rail 104 has a more flattened rectangular shape in cross-section, with the cross-sectional shape being uniform or constant along an entirety of the stent post frame 100 (but exhibiting the approximately 90 degree turn (e.g., within 5 degrees of a truly 90 degree turn) at a corresponding tip 110a-110c of each of the stent posts 106a-106c). Further, the cusp segments 108a-108c collectively define an elevated diameter.

Figure 6B:
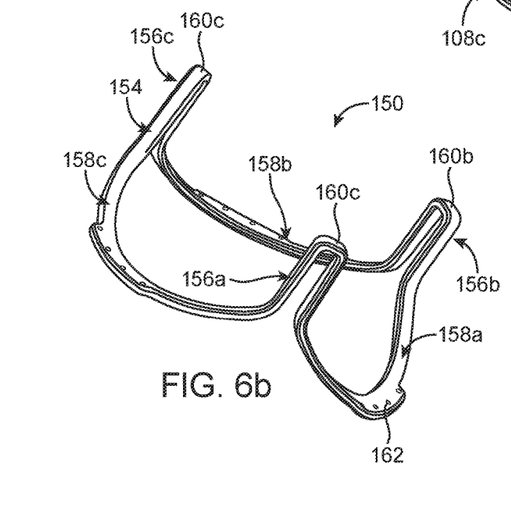
FIG. 6B is a perspective view of another stent post frame useful with the stented prosthetic heart valve of FIG. 1.
Figure 6C:
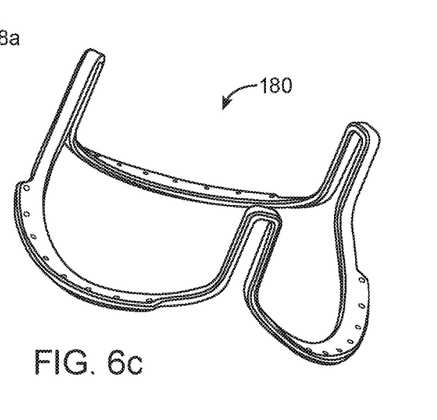
FIG. 6C is a perspective view of another stent post frame useful with the stented prosthetic heart valve of FIG. 1.

Another embodiment stent post frame 150 useful with the stented prosthetic heart valves of the present disclosure is shown in FIG. 6B. The stent post frame 150 is akin to previous embodiments, and has a continuous, closed-curve shape generated by a rail 154. The closed-curve shape includes three (optionally two) stent posts 156a-156c interposed between cups segments 158a-158c. The rail 154 again has a uniform cross-sectional shape along at least the stent posts 156a-156c, with the cross-sectional shape being non-circular and non-square (e.g., a simple rectangle), and exhibits the approximately 90 degree turn at a corresponding tip 160a-160c of each of the stent posts 156a-156c, and at a transition from the stent posts 156a-156c to the cusp segments 158a-158c as described above. The uniform or constant cross-sectional shape of the rail 154 continues along at least a portion of each of the cusp segments 158a-158c in extension from the corresponding stent posts 156a-156c. However, a flange 162 (identified for the first cusp segment 158a in FIG. 6B) is formed by the rail 154 along a central portion each of the cusp segments 158a-158c as a radially outward increase in the major axis dimension. The flange 162 provides increased surface area for attachment to the base frame 28 (FIG. 1). A circumferential length of the flange 162 can vary from that illustrated, as exhibited by a comparison of the stent post frame 150 of FIG. 6B with the alternative stent post frame 180 of FIG. 6C. As clarified by FIGS. 6B and 6C, in some embodiments the rails of the present disclosure can have a varying cross-sectional shape, for example along the cusp segments 158a-158c.

Returning to FIG. 2A, regardless of an exact shape of the stent post frame 26, in some embodiments the rail 40 is a molded plastic body, such as a single injection molded polyether ether ketone (PEEK) substrate. Other biocompatible polymers and manufacturing techniques (e.g., machining) are also envisioned. In yet other embodiments, the rail 40 can be formed of a metal or metal alloy.

Figure 7:
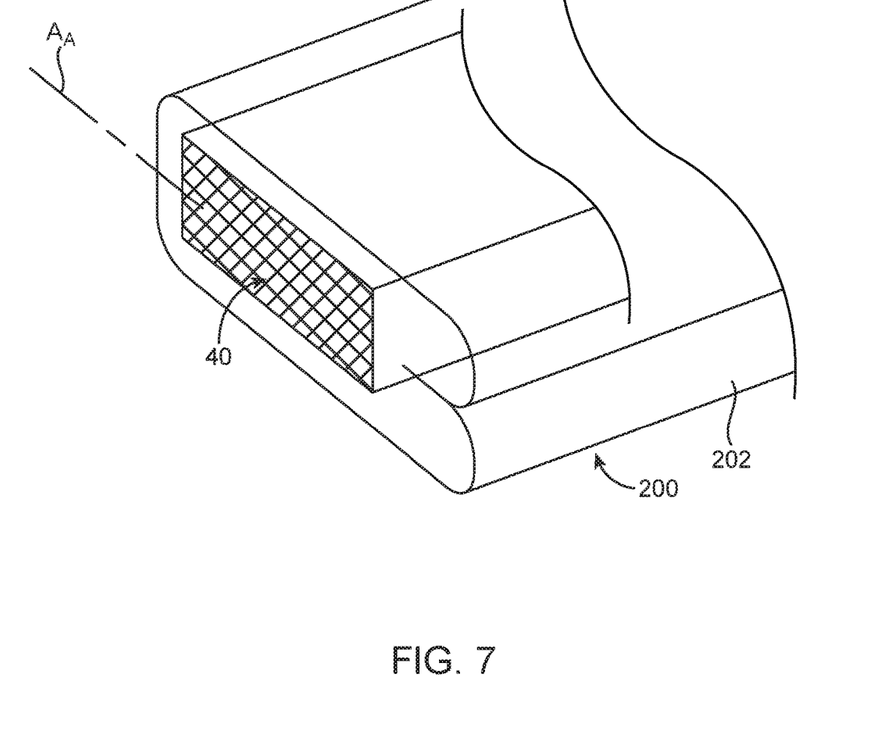
FIG. 7 is a simplified, cross-sectional view of a portion of a stent assembly of the prosthetic heart valve of FIG. 1, including a stent post frame and a stent post frame covering.

As mentioned above, stent post frame 26 is enveloped by a cloth covering. FIG. 7 provides a simplified illustration of one embodiment of a stent covering 200 surrounding the rail 40. The stent covering 200 can have a tubular or folded shape, and generally mimics the cross-sectional shape of the rail 40. In this regard, the stent covering 200 is assembled to or formed about the rail 40 so as to define a flange region 202. The flange region 202 represents an enlarged surface area of the stent covering 200 along the major axis $A_A$, and is located at the "exterior" side (radially outward side) of the stent post frame 26. In other words, and with additional reference to FIG. 2A, the flange region 202 is located radially opposite the longitudinal axis $L_A$, and provides an enlarged area for connection with the base frame 28 (FIG. 1) as described below. Regardless, the stent covering 200 can be formatted and assembled to the stent post frame 26 such that the stent covering 200 can freely rotate about the rail 40.

Figure 2A:
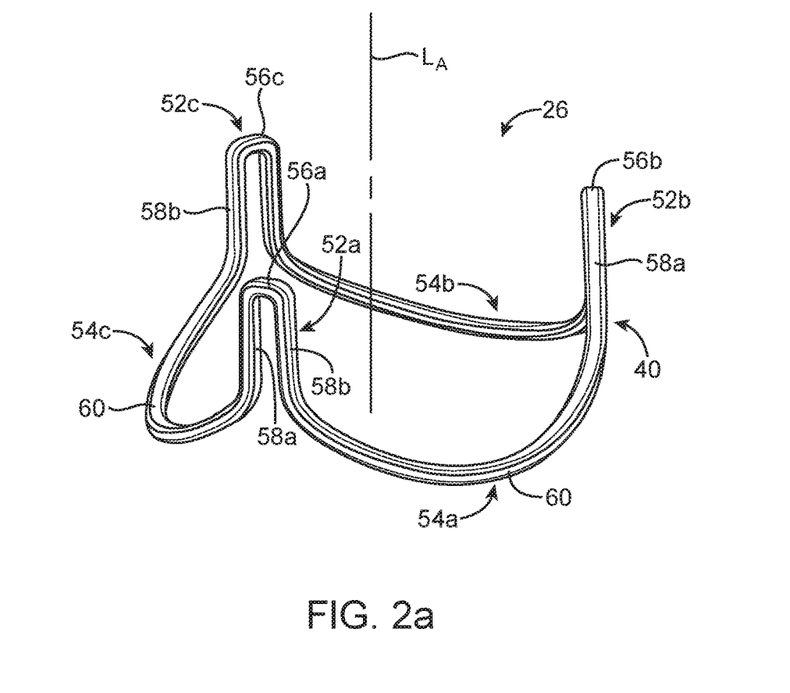
FIG. 2A is a perspective view of a stent post frame component of the prosthetic heart valve of FIG. 1.
Figure 2B:
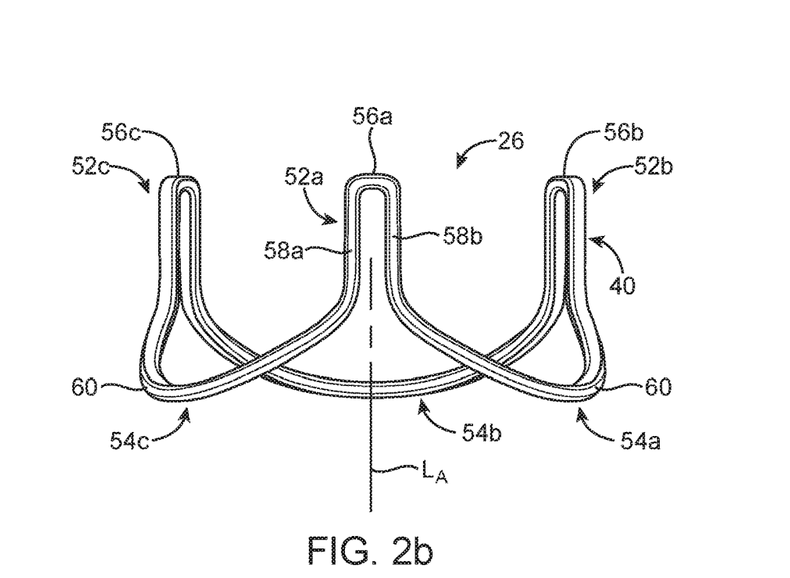
FIG. 2B is a side view of the stent post frame of FIG. 2A.
Figure 2C:
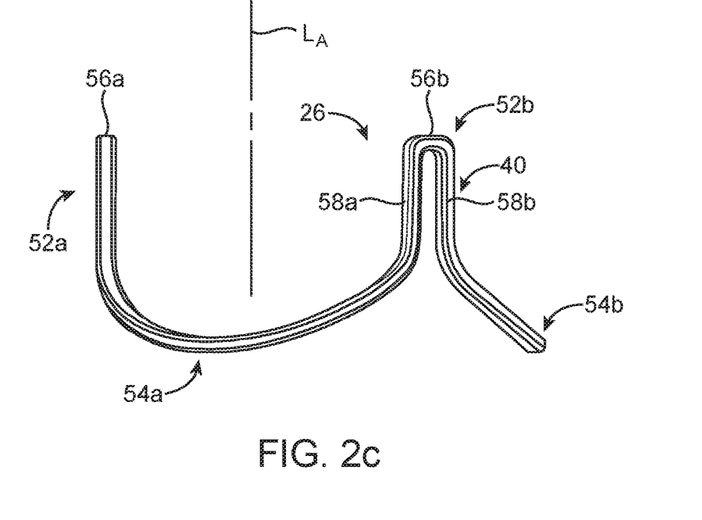
FIG. 2C is another side view of the stent post frame of FIG. 2A from a perspective differing from that of the view of FIG. 2B.
Figure 2D:
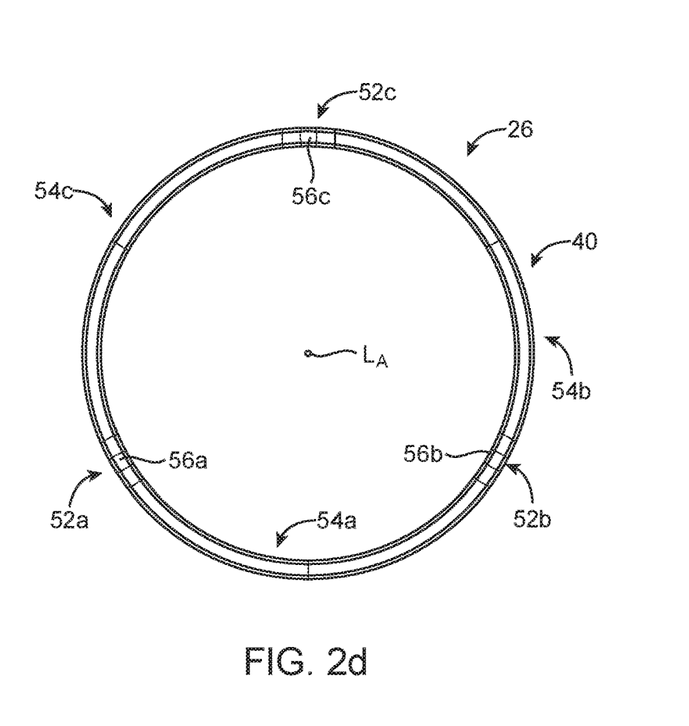
FIG. 2D is a top view of the stent post frame of FIG. 2A.
Figure 8A:
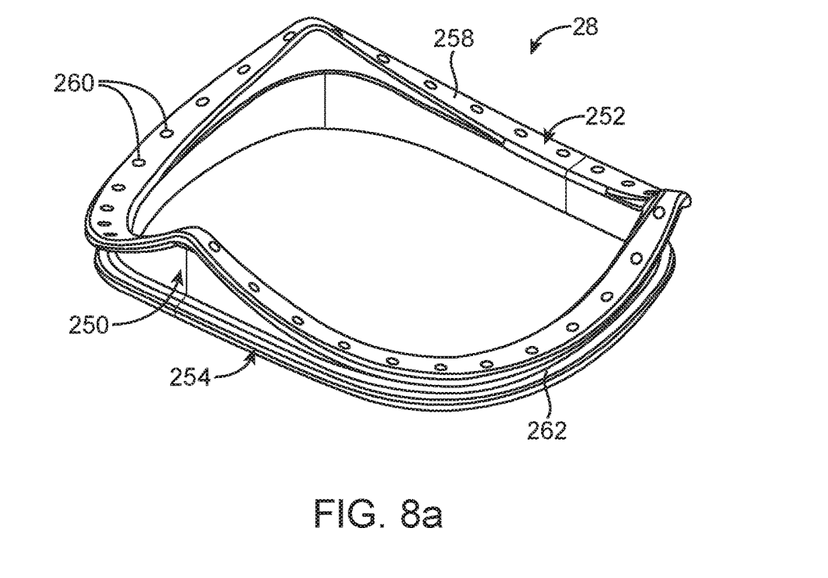
FIG. 8A is a perspective view of a base frame component of the prosthetic heart valve of FIG. 1.
Figure 8B:
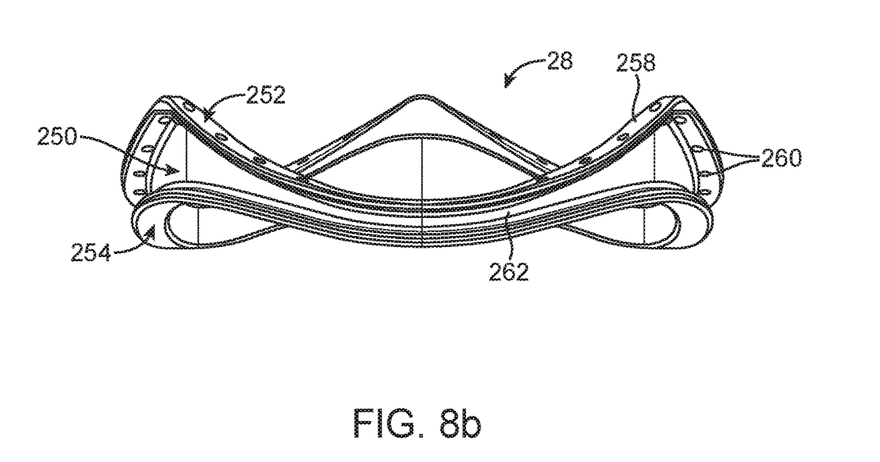
FIG. 8B is a side view of the base frame of FIG. 8A.

Returning to FIG. 1, the base frame 28 is generally configured to support the stent post frame 26. One embodiment of the base frame 28 is shown in greater detail in FIGS. 8A and 8B, and includes a hub 250, a support wall 252, and a lower flange 254. The hub 250 has a generally ring-like shape, mimicking the size, shape, and contours of the wireform 50 (FIG. 2A). Thus, a shape of the hub 250 generally follows the curvature of the cusp segments 54a-54c (FIG. 2A), and includes raised regions 256 that generally correspond to the stent posts 52a-52c (FIG. 2A).

The support wall 252 projects transversely outwardly from the hub 250 opposite the lower flange 254, and provides a smooth engagement face 258 having an enhanced surface area for connection to other components. In this regard, the support wall 252 can incorporate various connection features, such as pre-formed suture holes 260, which promote robust attachment as described below. As shown, the support wall 252 can have a profile that facilitates continuous interface (or direct contact) with the stent post frame 26 along the cusp of the leaflets 30-34 (FIG. 1).

The lower flange 254 can have a scallop-like profile, with a lower edge of the profile promoting increased section inertia and increased rigidity against crushing. Further, the lower flange 254 can incorporate various features that facilitate assembly of a sewing ring or cuff (not shown), for example by defining, in combination with the support wall 252, a groove 262. In other embodiments, the lower flange 254 can be omitted.

The base frame 28 can be formed from a variety of robust, biocompatible materials. In some embodiments, the base frame 28 is a single injection molded substrate (e.g., PEEK), although other materials (e.g., metal or metal alloys) and manufacturing techniques (e.g., machining) are also acceptable.

Figure 9:
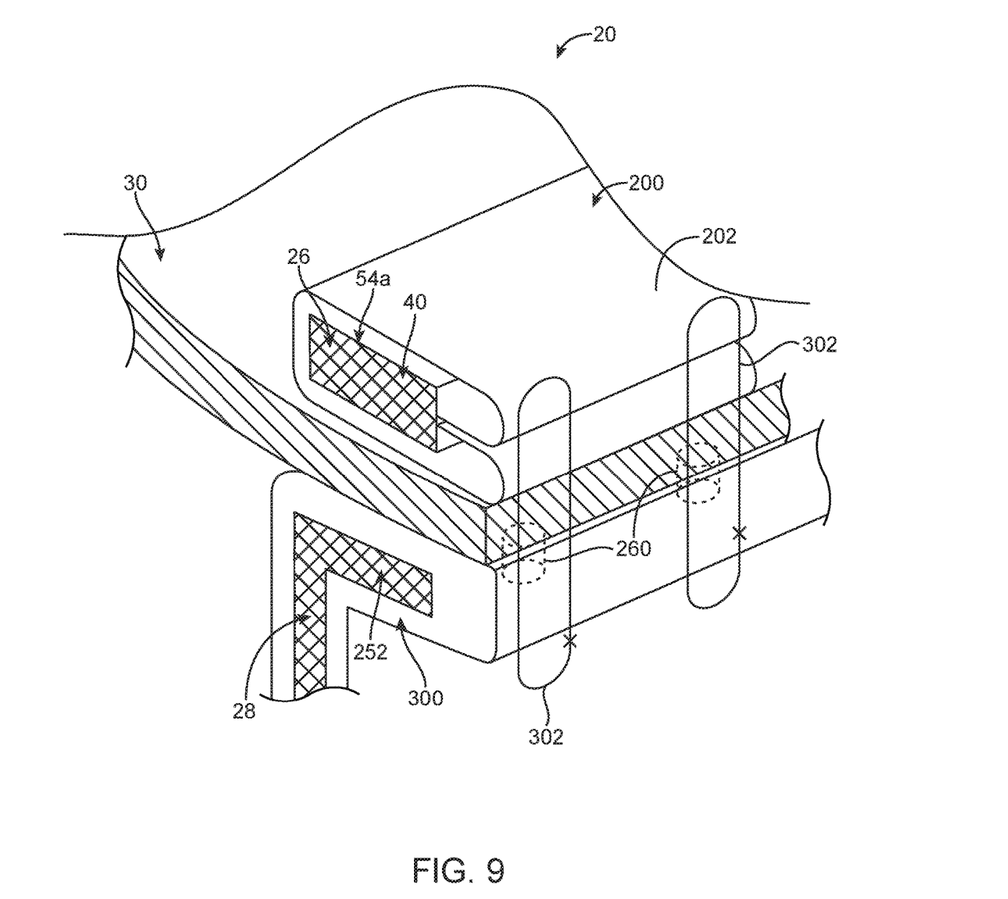
FIG. 9 is a simplified, cross-sectional view of a portion of the stented prosthetic heart valve of FIG. 1 upon final assembly.

Returning to FIG. 1 and as mentioned above, the base frame 28 is, in some embodiments, enveloped by a biocompatible cloth-like fabric akin to the stent post frame covering 200 (FIG. 7). With this in mind, the stented prosthetic heart valve 20 is assembled, in some embodiments, by attaching the valve leaflet assembly 24 between the stent post frame and base frame 26, 28. For example, FIG. 9 illustrates a portion of the stented prosthetic heart valve 20 upon final construction, including one of the leaflets 30, the first cusp segment 54a of the stent post frame 26, and a corresponding region of the base frame 28. As shown, the base frame 28 is encompassed by a cloth covering 300. The leaflet 30 is disposed between the stent post frame covering 200 and the base frame covering 300. Mounting members (e.g., sutures) 302 pass through the flange region 202 of the stent post frame covering 200, the leaflet 30, and the pre-formed holes 260 in the support wall 252 of the base frame 28. The tension of the sutures 302 effectively continuously "clamps" the leaflet 30 between the stent post frame 26 and the base frame 28. Notably, the sutures 302 are "behind" the rail 40 (i.e., the sutures 302 are not directly attached to the stent post frame 26), and thus no local demand is placed on the sutures 302 or the leaflet 30. Additional locking sutures (not shown) can be introduced to reinforce the base frame 28, thereby better ensuring that the rail 40 and the base frame 28 do not loosen relative to one another over time in a manner that might otherwise allow the leaflet cusp to begin to dilate in the radial direction. By providing the separate coverings 200, 300, clamping of the tissue leaflets 30-34 there between can be more robust in part because of the increased friction provided by the cloth of the coverings 200, 300 "biting" into the leaflets 30-34. Returning to FIGS. 1 and 2A, the gap 70 provided between the opposing legs 58a, 58b of each of the stent posts 52a-52c is sufficiently sized such that two adjacent ones of the leaflets 30-34 can be clamped between the legs 58a-58b as they are sutured together.

Figure 10:
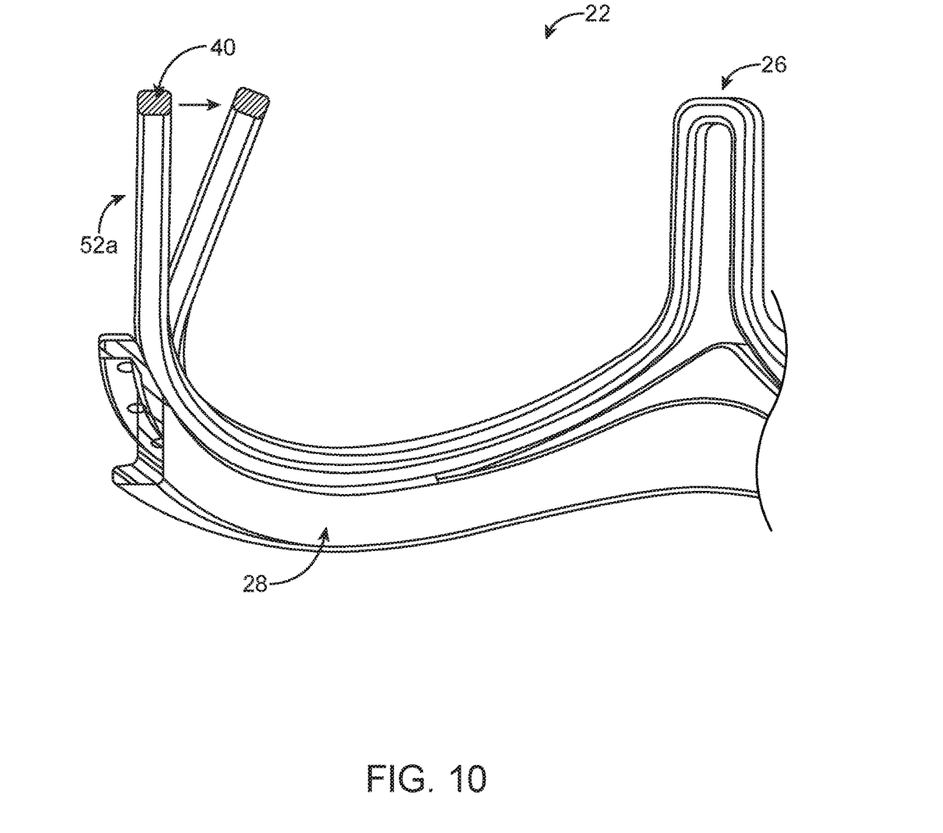
FIG. 10 is a cross-section view of a portion of the prosthetic heart valve of FIG. 1 and illustrating linear deflection of a stent post.

With the above construction, the desired "wishbone" bending characteristics are promoted by the manner which the cusp segments 54a-54c are constrained (i.e., connected to the base frame 28). If the rail 40 were considered to be encastre (rigid), there would be a considerable concentration of demand at the cusp segment center points 60 due to the rapid change in the torsion of rigidity of the system in transitioning from the freely bending stent post tips 56a-56c to the rigid cusp segment center points 60. By more lightly constraining the cusp segments 54a-54c in a manner that effectively prevents lateral deflection in the horizontal plane, the entire stent assembly 22 is active in the structural response and significantly reduces the demand on the cross-sectional shape of the rail 40. The base frame 28 applies a continuous boundary condition to the lower margins of the stent post frame 26. As a result, the stent posts 52a-52c experience linear deflection in response to external forces, as illustrated in FIG. 10.

The stent prosthetic heart valves and corresponding methods of manufacture of the present disclosure provide a marked improvement over previous designs. By incorporating a compound cross-sectional shape for the stent post frame rail and spatially arranging the cross-sectional shape in a desired manner along the stent post frame, the relative rigidity of the stent is controlled, and a pre-defined bending direction can be achieved. Further, attaching the valve leaflets directly to a structure of the base frame and indirectly to the stent post frame (via a separate covering) promotes robust leaflet attachment while not overtly constraining the stent post frame.

Although the present disclosure has been described with reference to preferred embodiments, workers skilled in the art will recognize that changes can be made in form and detail without departing from the spirit and scope of the present disclosure.

What is claimed is:

1. A stented prosthetic heart valve comprising:
a stent post frame including a continuously formed rail forming a closed-curve shape defining a central longitudinal axis, the closed-curve shape including a plurality of circumferentially-spaced posts projecting from, and interposed between cusp segments in a direction of the longitudinal axis, the rail defining a major axis and a minor axis perpendicular to the major axis, the rail having a major axis dimension greater than a minor axis dimension;
wherein a first one of the posts is defined by spaced apart, first and second leg portions and a tip, the first leg portion extending from a first one of the cusp segments to the tip, the second leg portion extending from a second one of the cusp segments to the tip, and further wherein the stent post frame is configured such that the first leg portion is free of connection to the second leg portion apart from the tip;
a stent post frame cloth covering encompassing the rail;
a base frame configured to support the cusp segments of the stent post frame, the base frame including a hub and a support wall extending transversely outwardly from the hub relative to the central longitudinal axis; and
a valve leaflet assembly connected to the stent post frame and including a first leaflet clamped between the first one of the cusp segments and the support wall wherein a gap is defined between the first and second leg portions, and further wherein the first leaflet and a second leaflet of the valve leaflet assembly are within the gap and are clamped between the first and second leg portions;
wherein the major axis of the rail is parallel to an engagement face of the support wall along the cusp segments wherein the engagement face is configured to continuously interface with the stent post frame along the cusp segments.

2. The stented prosthetic heart valve of claim 1, wherein the major axis is rotated approximately 90 degrees along the stent posts from the cusp segments.

3. The stented prosthetic heart valve of claim 1, wherein the rail has the constant cross-sectional shape along an entirety of the stent post frame.

4. The stented prosthetic heart valve of claim 1, wherein the stent post frame cloth covering extends between a lower face of each of the cusp segments and the engagement face of the support wall.

5. The stented prosthetic heart valve of claim 1, wherein the stent post frame consists of only the rail.

6. The stented prosthetic heart valve claim 5, wherein the stent post frame cloth covering encompasses only the stent post frame.

7. The stented prosthetic heart valve of claim 1, wherein stented prosthetic heart valve is configured such that stent post frame does not physically contact the base frame.

8. The stented prosthetic heart valve of claim 1, wherein the support wall defines a hole, the stented prosthetic heart valve further comprising a suture passing through the stent post frame cloth covering, the first leaflet and the hole.

9. The stented prosthetic heart valve of claim 1, wherein a terminal edge of the first leaflet along that region of the first leaflet otherwise clamped between the first one of the cusp segments and the support wall is exposed relative to the base frame.

10. The stented prosthetic heart valve of claim 9, wherein the terminal edge is uncovered.

* * * * *